Figure 1:
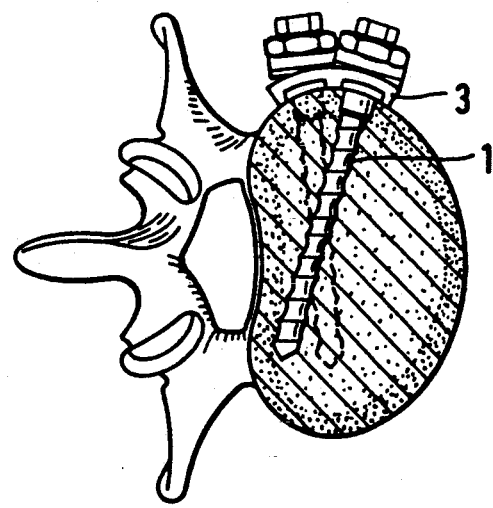

United States Patent [19]
Keller

[11] Patent Number: 5,234,431
[45] Date of Patent: Aug. 10, 1993

[54] BONE PLATE ARRANGEMENT

[75] Inventor: Arnold Keller, Kayhude, Fed. Rep. of Germany

[73] Assignee: Waldemar Link GmbH & Co., Hamburg, Fed. Rep. of Germany

[21] Appl. No.: 862,221

[22] Filed: Apr. 2, 1992

[30] Foreign Application Priority Data

Apr. 3, 1991 [DE] Fed. Rep. of Germany ... 9104025[U]

[51] Int. Cl.[5] .......................... A61F 5/04; A61F 2/44
[52] U.S. Cl. ........................................ 606/70; 606/61; 606/69; 623/17
[58] Field of Search .................. 606/69, 60, 70, 61, 606/71, 72, 73; 623/17

[56] References Cited

U.S. PATENT DOCUMENTS

| | | | |
|---|---|---|---|
| 4,696,290 | 9/1987 | Steffee | 606/73 |
| 4,887,595 | 12/1989 | Heinig et al. | 606/73 |
| 5,085,660 | 2/1992 | Lin | 606/73 |

FOREIGN PATENT DOCUMENTS

| | | |
|---|---|---|
| 0077681 | 4/1983 | European Pat. Off. . |
| 0085493 | 8/1983 | European Pat. Off. . |
| 0241914 | 10/1987 | European Pat. Off. . |
| 0410309 | 1/1991 | European Pat. Off. . |
| 251246 | of 1911 | Fed. Rep. of Germany . |
| 3027138 | 12/1981 | Fed. Rep. of Germany . |
| 0782462 | 6/1935 | France ................................. 606/73 |
| 2178323 | 2/1987 | United Kingdom ................... 606/61 |
| WO9012547 | 11/1990 | World Int. Prop. O. . |

Primary Examiner—David Isabella
Attorney, Agent, or Firm—Chilton, Alix & Van Kirk

[57] ABSTRACT

A bone plate arrangement consisting of a bone plate with at least one through-opening and a bone screw to be introduced into the through-opening. The bone screw is held in the bone plate by means of a sleeve, which can be fixed in the through-opening of the bone plate independently of the screw. The sleeve can be designed in such a way that it predetermines the angular orientation of the screw relative to the bone plate. If the through-opening in the bone plate is elongate, the position of the bone screw along the through-opening can also be predetermined by the positioning of the sleeve.

16 Claims, 4 Drawing Sheets

BONE PLATE ARRANGEMENT

Bone plate arrangements are known, especially for spinal surgery, which allow a fixed angular relation between bone screw and bone plate to be produced, for example in order to give a bone fragment or a vertebra a predetermined angular position in relation to adjacent fragments or vertebrae (EP-PS 0,201,024, EP-OS 0,242,842). In these cases, the position at which the bone screw passes through the bone plate is established by the bore arrangement in the bone plate. The known arrangements are also very thick. Moreover, the bone plate can obstruct the view of and the access to the position at which a bone screw is to be fitted. Finally, a good many known bone plate arrangements have the disadvantage that the connection between bone plate and screw loosens if the screw slackens in the bone, in which case there is also a risk of the screw working its way right through the bone plate and out. This is also true of a known arrangement (EP-A-0,410,309) in which the semispherically designed head of the screw rests in the spherical recess of a supporting plate, which in turn can be adjusted on an oblong-shaped through-opening of the bone plate and is held in the desired position by interaction of ribbing.

The object of the invention is therefore to provide a bone plate arrangement of the type mentioned in the introduction, which affords a greater degree of freedom when fitting the screw and better access to the bone, and which remains at a steady angle even if the screw slackens in the bone, in which respect the outward movement of this slackening screw is prevented. The solution according to the invention consists of the features in the claims.

The invention in a preferred form is a bone plate arrangement which has a bone plate including at least one through-opening, a bone screw to be introduced into the through-opening, and a sleeve which can be fixed in the through-opening separately from the bone screw. The bone screw can be fixed in the sleeve.

By virtue of the fact that the sleeve can be fixed on the bone plate independently of the fitting of the bone screw, the angular position of the bone screw relative to the bone plate and/or the position of the bone screw along an oblong hole provided in the bone plate can be determined independently of the introduction of the bone screw into the bone.

For this purpose, the sleeve can be designed in such a way that it can be connected to the plate at a defined and fixed angle, the stability of the angle between bone screws and sleeve being guaranteed by virtue of the fact that the through-opening in the sleeve can be of any desired length and can be made to match the diameter of the screw shaft. A sleeve design which is particularly simple and advantageous is one in which there is provided at one end a thread for receiving a nut to be supported on one side of the bone plate, and near the other end a counterflange for supporting on the other side of the bone plate. As soon as it has been established where on the bone plate the screw is to be connected to the latter, the sleeve can be screwed tightly to the bone plate. After the screw has been fitted, the bone plate and the sleeve provided thereon are arranged on the screw.

The counterflange of the sleeve is advantageously designed in such a way that it presents a plane surface to the bone plate, by means of which plane surface the angular position of the sleeve relative to the plate is formed. A right-angled arrangement is generally desired, so that the counterflange extends at right angles to the sleeve. If an oblique arrangement of the screw relative to the bone plate is intended, it is instead possible to provide a correspondingly angled arrangement of the counterflange on the sleeve. According to the invention it is intended that the bone plate hole (or bone plate holes) provided for receiving the sleeve should at least in one direction be wider than the outer sleeve diameter, so that the sleeve can be displaced in this hole in at least one direction. Positive positioning of the sleeve relative to the bone plate can then be effected by means of clamping on the plate surfaces. According to the invention, this is improved by virtue of the fact that at least one side of the bone plate and the cooperating surface of a supporting plate, connected to the sleeve, or of the counterflange of the sleeve are of roughened design matching one another. If the bone plate holes are designed as oblong holes, the surface roughness is advantageously made up of grooves extending transverse to the oblong hole direction in order to afford better resistance to the displacement in the oblong hole direction, while the positioning can be effected transverse to this direction through the oblong hole itself.

If it is desired to be able to freely adjust the angle of the bone screw relative to the bone plate, according to the invention it is possible to provide in the nut-side and counterflange-side supporting of the sleeve on the bone plate in each case one spherical supporting surface, and at least on one side the supporting force can be transmitted by means of a displaceable supporting plate bearing on the bone plate via a roughened surface. For example, if a free positioning of the bone screw in a surface direction of the bone plate is not required, the through-hole in the bone plate can cooperate with a spherically convex surface of the counterflange of the sleeve, whereas on the other side the convexly spherical lower surface of the nut cooperates with a supporting plate which in turn, like the top side of the bone plate, is provided with a roughened surface. If, in contrast, a displaceability of the screw in a surface direction of the bone plate is desired, the convexly spherical surface of the counterflange does not cooperate directly with the bone plate, but instead with a supporting plate which in turn cooperates with the lower side of the bone plate via a roughened surface According to a further feature of the invention, the bone screw has, for the purpose of connection to the sleeve, a journal to be accommodated in the sleeve bore, and has between the journal and the thread a collar and, at the end of the journal remote from the collar, a securing member which can be made up of a thread at the end of the bolt and a nut. Whereas conventional screws having a head cannot be screwed in until the bone plate has been arranged on the bone, this design permits a procedure in which the screw(s) is (are) fitted first, and only then is the bone plate arranged on the screw(s). The plate does not therefore obstruct access to the bone when the screw is being fitted. The arrangement also remains as a solid unit per se, even if a screw slackens in the bone. In particular, the distances and the angular positions of screws connected to the same bone plate are maintained. Finally, it is also impossible for a screw, once it has slackened in the bone, to move out from the bone plate arrangement.

According to a further feature of the invention, it is possible for the screw to be turned even after connection to the bone plate. When fitting the screw, it may not be possible under certain circumstances to estimate the necessary height of the screw relative to the bone surface with sufficient precision, and the screw is therefore deliberately inserted to a lesser depth than is expected to be necessary. Only after the nut has been connected to the bone plate is the screw screwed in until the bone plate takes up the desired position on the surface of the bone. In this way it is possible to ensure that the bone plate does not bear with pressure on the surface of the bone, as a result of which, according to the invention, the risk of slackening can be further reduced. Whereas in the case of known arrangements the bone screw is constantly affected by the counterforce which compensates the pressure of the bone plate on the surface of the bone, as a result of which, even in the immobilized state, a bone degeneration can take place in the area of the threads and thereby cause slackening, the arrangement according to the invention is free from such forces in the immobilized state.

The stated rotatability of the bone screw after its connection to the bone plate can be ensured, when the bone screw is secured by means of a nut on the sleeve, by virtue of the fact that the thread provided at the bolt end for receiving the nut is dimensioned so short that a fixed bearing of the nut on the sleeve does not come about. To turn the screw, a tool can then be applied to the nut. Instead, it would of course also be possible to use wrench surfaces provided on the screw shaft. However, in general, measures of this type are not necessary since the screw normally remains rotatable, at any case in the screwing-in direction, by means of a tool applied to the nut when the nut has come to bear completely on the bone plate or on a part connected to it.

The bone plate can, as is known per se, be curved in the transverse direction in order to be able to be connected more stably to bone surfaces of corresponding curvature.

Figure 2:
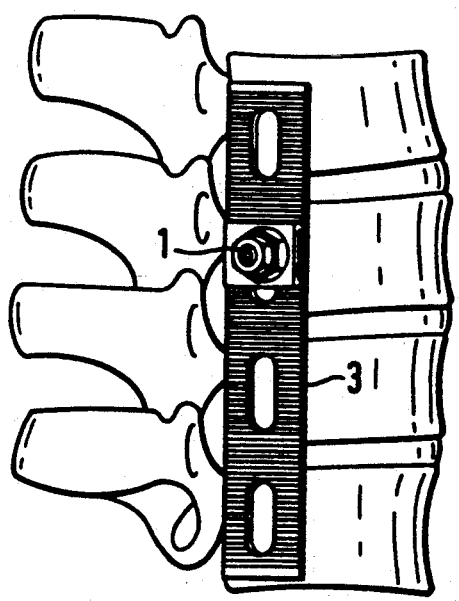
Figure 3:
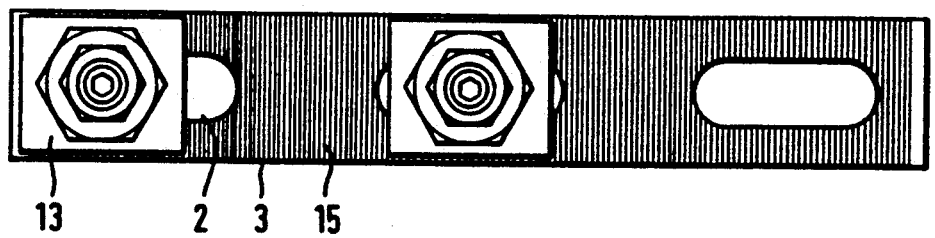
Figure 4:
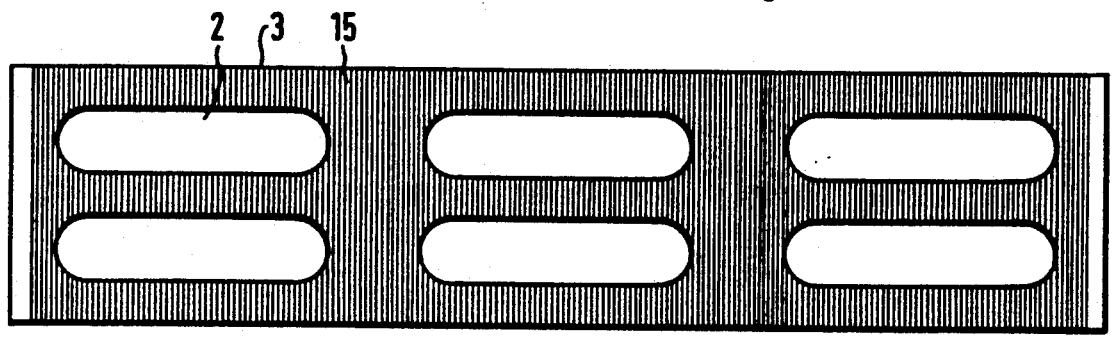
Figure 5:
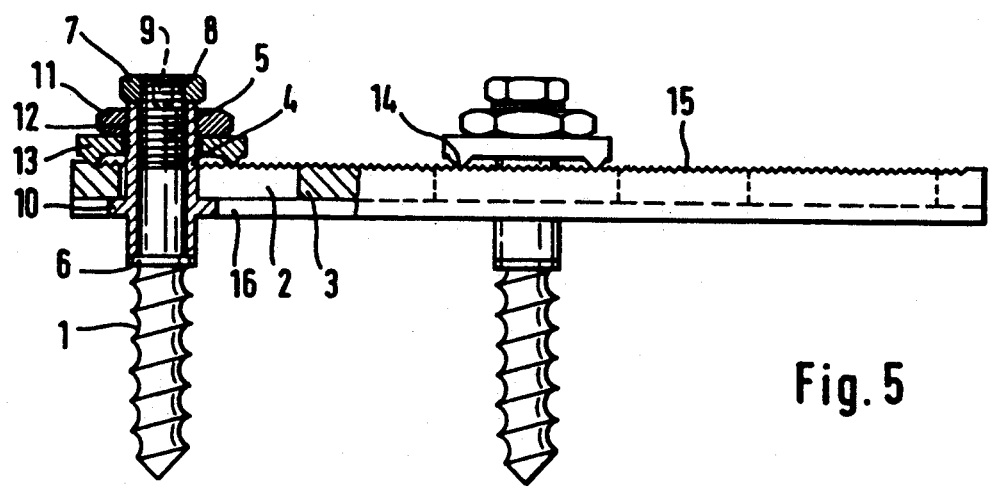
Figure 6:
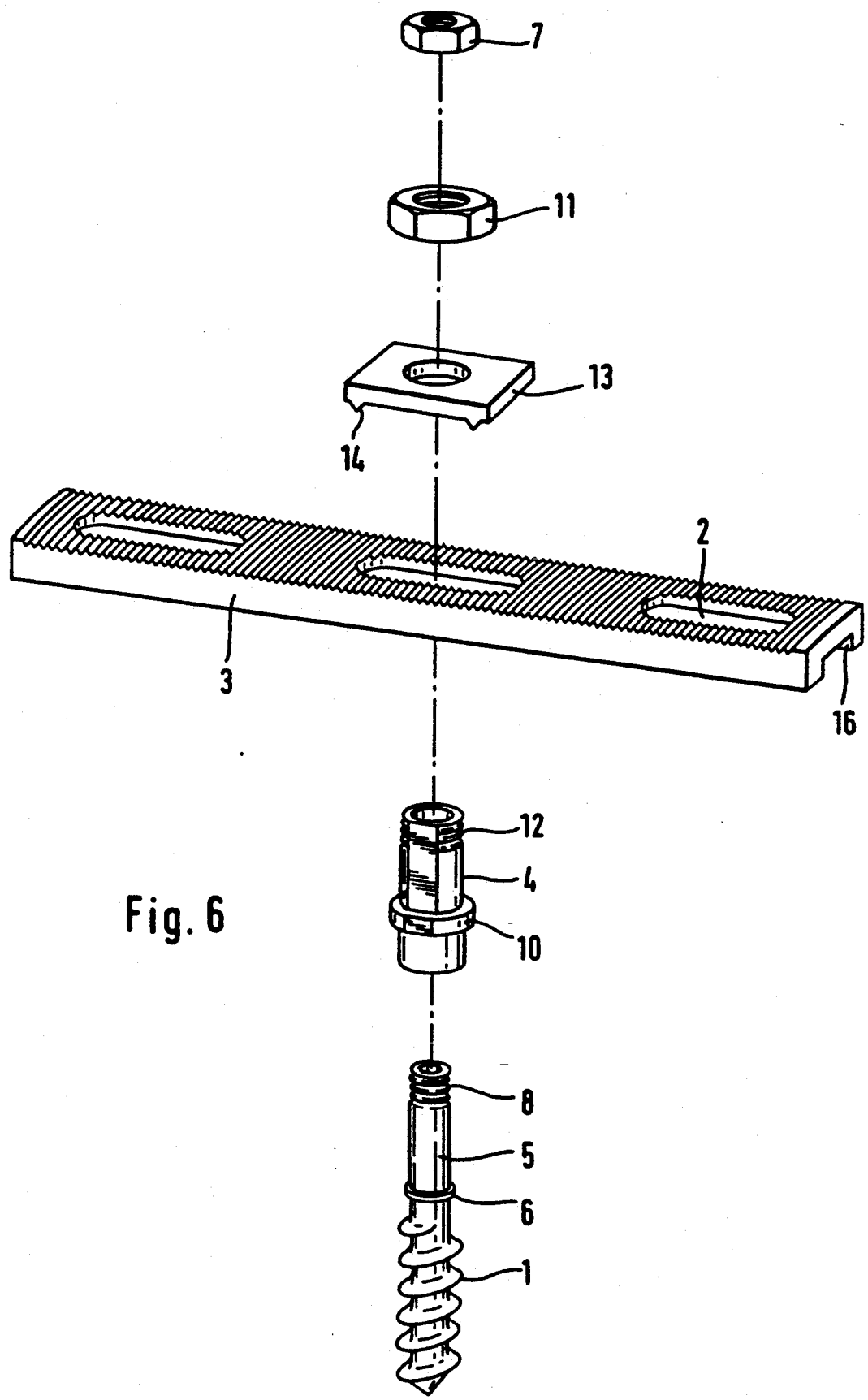
Figure 7:
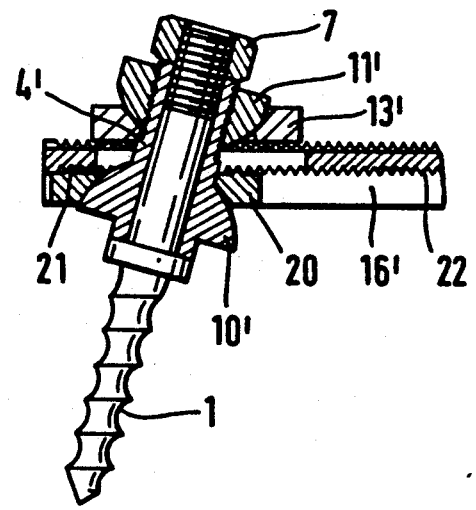
Figure 8:
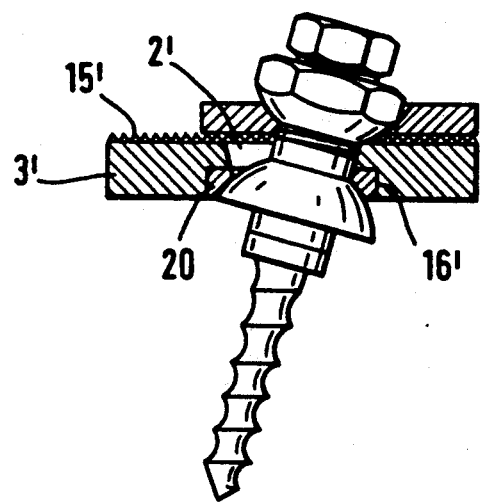
Figure 9:
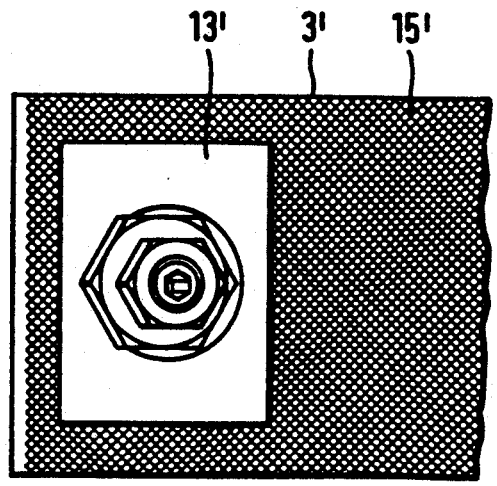

The invention is described in greater detail hereinbelow with reference to the drawing, in which advantageous exemplary embodiments are shown and in which, FIG. 1 shows a vertical view of the arrangement arranged on a vertebra, FIG. 2 shows a side view of a similar arrangement, FIGS. 3 and 4 show a bone plate with one row/two rows of oblong holes, FIG. 5 shows a partially cutaway side view of the bone plate arrangement, FIG. 6 shows an exploded representation of the elements involved, FIGS. 7 and 8 show an angularly adjustable arrangement, and FIG. 9 shows a plan view.

FIGS. 1 and 2 show the arrangement applied laterally on a series of vertebrae, as may be necessary in ventral spinal surgery. The bone plate is curved in the transverse direction in order to be better adapted to the contour of the spine. In other applications this may be unnecessary In FIG. 1 it is assumed that the bone plate, as illustrated in FIG. 4, has two rows of oblong holes in order to permit an offset screw arrangement in two rows of screws, whereas the bone plate illustrated in FIGS. 2 and 3 has only one row of oblong holes.

The bone screws 1 are held in the oblong holes 2 of the bone plates 3 by means of sleeves 4 whose bore corresponds with appropriate play to the diameter of the shaft 5 of the bone screws. For securing in the sleeves, the bone screws are equipped in each case with a collar 6 and a nut 7, which sits on a thread 8 arranged at the end of the shaft 5. So that it can be screwed independently, the bone screw has a hexagon socket 9 at the end.

For the purpose of connection to the bone plate 3, the sleeve has a counterflange 10 and a nut 11 on a thread 12. The nut 11 is supported on the top side of the bone plate 3 via a supporting plate 13 which has on its underside two blade-shaped raised parts 14 extending transverse to the plane of projection of FIG. 5. The top side of the bone plate is grooved transverse to the direction of the oblong holes 2, as indicated by 15, and the blades 14 engage in the grooves 15, as a result of which the supporting plate 13 is prevented from being displaced in the direction of the oblong holes 2 when the nut 11 is being tightened. These blades and grooves form the roughened surface mentioned hereinabove. At the same time the counterflange 10 bears on the underside of the bone plate 3, in which respect it lies inside a groove 16 which receives it with an exact fit. The sleeve 4 and the counterflange 10 are flattened at the sides, as can be seen more clearly in FIG. 6, the flattened areas 17 cooperating with the flanks of the oblong holes 2 and the groove 16 in order to prevent the sleeve 4 from turning when the nut 11 is tightened or loosened.

Characteristic of the procedure for the operation is the fact that the screws are fitted first, in which respect the bone plate (with or without sleeves secured thereon) can be used in the manner of a hole gauge. A guide instrument can be provided for pre-drilling at the correct angle. Instead of this, sleeves 4 arranged on the bone plate can also serve at the intended positions as a guide for the further pre-drilling at the correct angle, if the angular position of the bone fragment or spine relative to the plate is not intended to be altered.

Then, via the shaft 5 of the screwed-in bone screw, the hole in the vertebra is drilled further open by means of a hollow cutter for accommodating the bone-side end of the sleeve 4. At the same time the depth of fit of the bone screw in the vertebra can be checked.

Before this has been done, the sleeves are connected to the bone plate. The bone plate together with the sleeves is then fitted onto the shafts of the screws introduced into the bone, and the screws are secured using the nuts 7. The connection of the sleeves 4 to the bone plate can (but need not) still be loose at this stage in order to permit a lengthwise correction (distraction, extraction) by means of the bone screws introduced. A special instrument can be provided for this purpose. The nuts 11 are then tightened securely. In this way an angularly stable protection of the bone screws is achieved, even in the case of a possible slackening in the bone. Finally, if appropriate, the screws 1 are then screwed further into the bone, by applying a tool to the nuts 7 or to the hexagon socket 9, until the bone plate 3 bears on the surface of the bone.

FIGS. 7 and 8 show a longitudinal section and a cross-section through a similar arrangement, which also permits an oblique positioning of the screws relative to the bone plate. The counterflange 10, of the bone screw 1 is of convexly spherical design on the side facing away from the bone, the sphere centers being at a great distance from one another. The same applies conversely to the nut 11'. The counterflange 10, cooperates with a pressure plate 20, which is displaceable in the longitudinal direction in the groove 16, on the underside of the bone plate and has two blades 21 (analogous to the blades 14 of the supporting plate 13) which cooperate with a transverse grooving 22 on the bottom of the groove 16, The spherical surface of the nut 11, cooperates with a corresponding, concavely spherical surface of the supporting plate 13'. The underside of the supporting plate 13, and the top side 15, of the bone plate are roughened, to be precise, as indicated in FIG. 9, by grooves extending transversely to one another, so that a plurality of discrete pyramidal raised parts are formed. In this way the supporting plate 13, can be displaced not only in the longitudinal direction, but also in the transverse direction relative to the bone plate 3, and can be fixed by tightening the nut 11,. In contrast, the pressure plate 20' can be displaced in the groove 16' only in the longitudinal direction. The hole 2' in the bone plate 3' is wider than the outer diameter of the sleeve 4' not only in the longitudinal direction, but also in the transverse direction. In addition to the offset and angled arrangement of the screw in a longitudinal plane (FIG. 7), an angular adjustment can therefore also be carried out in a transverse plane (FIG. 8). The manipulation corresponds essentially to what has been discussed above.

I claim:

1. A bone plate arrangement, comprising:
a bone plate having generally opposite first and second sides and an opening therethrough,
a sleeve to be fixed in the bone plate opening, the sleeve having a bore, a pair of opposite ends, a threaded portion at one end for receiving a nut to be supported on the first side of the bone plate, an a counterflange at the opposite end to be supported on the second side of the bone plate, and
a bone screw to be fixed in the sleeve separately from the fixation of the sleeve in the bone plate opening, the bone screw having a longitudinal axis, longitudinally spaced first and second ends, a threaded portion at the first end to be received in a bone, a securing member at the second end for securing the bone screw to said screw, a shaft portion between the threaded portion and the securing member to be journalled in the sleeve, and a collar between the threaded portion and the shaft portion.

2. The bone plate arrangement as claimed in claim 1, wherein the arrangement includes means for fixing the sleeve in a predetermined angular relationship relative to the bone plate, said means including the counterflange and the threaded portion of the sleeve, and wherein the angular relationship of the longitudinal axis of the bone screw relative to the sleeve is determined by the sleeve bore.

3. The bone plate arrangement as claimed in claim 1, wherein the sleeve has a longitudinal axis, and the counterflange has a planar surface that engages the second side of the bone plate and forms an angle with the longitudinal axis, thereby defining the angular position of the sleeve relative to the bone plate.

4. The bone plate arrangement as claimed in claim 3, wherein the counterflange is arranged at a right angle to the sleeve.

5. The bone plate arrangement as claimed in claim 1, further including a supporting plate connected to the sleeve, the supporting plate having a roughened surface in contact with one of the first and second sides of the bone plate, wherein the bone plate opening is an oblong hole, and the side of the bone plate in contact with the supporting plate has a roughened surface which is complementary to the roughened surface of the supporting plate.

6. The bone plate arrangement as claimed in claim 1, wherein the securing member comprises a threaded segment and a bone screw nut.

7. A bone plate arrangement comprising a bone plate having opposite first and second sides and at least one aperture therethrough, a sleeve to be introduced into the aperture, and a bone screw to be fixed in the sleeve, the sleeve having a pair of longitudinally spaced ends, a threaded portion at one end for supporting a nut to be supported on the first side of the bone plate, and a counterflange at the other end to be supported on the second side of the bone plate, the bone screw including a shaft portion which has a pair of longitudinally spaced ends and is journalled for rotation within the sleeve, a threaded portion to be inserted into a bone, a collar between the journalled shaft portion and the threaded portion, and a securing member at the end of the journalled shaft portion which is furthest from the collar for securing the bone screw to said sleeve.

8. The bone plate arrangement as claimed in claim 7, further including a spherical supporting surface on at least one of the first and second sides of the bone plate, and a displaceable supporting plate for transmitting a first and second sides of the bone plate for transmitting a supporting force to the bone plate, the supporting plate having a roughened surface in contact with the bone plate.

9. The bone plate arrangement as claimed in claim 6 wherein the bone plate arrangement includes means for rotating the bone screw by rotating the bone screw nut.

10. The bone plate arrangement as claimed in claim 7, wherein the sleeve includes a bore having a first orientation and means including the threaded portion and the counterflange for fixing the sleeve at a predetermined angular position in the bone plate, and wherein the bone screw has an orientation which coincides with the first orientation of the bore when the bone screw is inserted in the bore.

11. The bone plate arrangement as claimed in claim 7, wherein the sleeve has a longitudinal axis, and the counterflange has a planar surface that forms an angle with the longitudinal axis, thereby defining the angular position of the sleeve relative to the bone plate.

12. The bone plate arrangement as claimed in claim 11, wherein the counterflange is perpendicular to the longitudinal axis of the sleeve.

13. The bone plate arrangement as claimed in claim 7, wherein the bone plate aperture is oblong, the bone plate arrangement further comprising a supporting plate threadably connected to the sleeve, the supporting plate having a cooperating surface for contacting a portion of the bone plate, and wherein the cooperating surface and the portion of the bone plate in contact with the cooperating surface are roughened to prevent movement of the supporting plate along the oblong dimension of the bone plate aperture.

14. The bone plate arrangement as claimed in claim 7, further comprising a selectively positionable supporting plate having a contact surface bearing against a side of the bone plate, the contact surface and the side of the bore plate contacting the supporting plate being roughened, wherein the sleeve is supported on at least one side of the bone plate by a spherical supporting surface.

15. The bone plate arrangement as claimed in claim 7, wherein the securing member is formed by a thread and a bone screw nut mounted on the thread.

16. The bone plate arrangement as claimed in claim 15, wherein the bone plate arrangement includes means for rotating the bone screw by rotating the bone screw nut.

* * * * *

UNITED STATES PATENT AND TRADEMARK OFFICE
CERTIFICATE OF CORRECTION

PATENT NO. : 5,234,431
DATED : August 10, 1993
INVENTOR(S) : Arnold Keller

It is certified that error appears in the above-indentified patent and that said Letters Patent is hereby corrected as shown below:

Claim 1, column 5, line 16, change "screw" (second occurance) to --sleeve--.

Claim 14, column 6, line 5, change "bore" to --bone--.

Signed and Sealed this

Thirtieth Day of August, 1994

*Attest:*

BRUCE LEHMAN

*Attesting Officer*     *Commissioner of Patents and Trademarks*